(12) United States Patent
Tsutsumi

(10) Patent No.: US 8,896,677 B2
(45) Date of Patent: Nov. 25, 2014

(54) IMAGING DEVICE AND TRANSMISSION/RECEPTION SYSTEM

(75) Inventor: Shinichi Tsutsumi, Kanagawa (JP)

(73) Assignee: Sony Corporation, Tokyo (JP)

( * ) Notice: Subject to any disclaimer, the term of this patent is extended or adjusted under 35 U.S.C. 154(b) by 606 days.

(21) Appl. No.: 13/157,448

(22) Filed: Jun. 10, 2011

(65) Prior Publication Data

US 2012/0007973 A1 Jan. 12, 2012

(30) Foreign Application Priority Data

Jul. 7, 2010 (JP) ................................ 2010-155045

(51) Int. Cl.
*A62B 1/04* (2006.01)
*A61B 1/00* (2006.01)
*A61B 1/04* (2006.01)

(52) U.S. Cl.
CPC ............... *A61B 1/041* (2013.01); *A61B 1/0002* (2013.01); *A61B 1/00016* (2013.01)
USPC ........................................................ 348/65

(58) Field of Classification Search
USPC ........................................................ 348/65
See application file for complete search history.

(56) References Cited

U.S. PATENT DOCUMENTS

| 8,165,374 | B1 * | 4/2012 | Wang et al. | 382/128 |
| 2006/0209185 | A1 * | 9/2006 | Yokoi | 348/65 |
| 2007/0098379 | A1 * | 5/2007 | Wang et al. | 396/14 |
| 2007/0167715 | A1 * | 7/2007 | Shigemori | 600/407 |
| 2008/0108866 | A1 * | 5/2008 | Lin | 600/103 |
| 2012/0101331 | A1 * | 4/2012 | Gilad et al. | 600/114 |

FOREIGN PATENT DOCUMENTS

| JP | 2009-153617 | 7/2009 |
| JP | 2009-178234 | 8/2009 |
| JP | 2009-189475 | 8/2009 |

OTHER PUBLICATIONS

Moglia et al., Recent Patents on Wireless Capsule Endoscopy, 2008, Center for Applied Research in Micro Engineering (CRIM Lab), pp. 1-10.*

Rakotondranibe et al., Millimeter-Wave System for High Data Rate Indoor Communications, May 2009, IETR-INSA, UMR CNRS 6164, pp. 1-4.*

* cited by examiner

*Primary Examiner* — Sath V Perungavoor
*Assistant Examiner* — Peter D Le
(74) *Attorney, Agent, or Firm* — Sony Corporatioin

(57) ABSTRACT

There are provided an inexpensive imaging device that may perform data transmission promptly and easily, and a transmission/reception system using the imaging device. The imaging device includes, an imaging section, a recording section storing data of images shot by the imaging section, a transmission section transmitting the data stored in the recording section to the outside by radio, and a controller controlling the transmission section to start data transmission after the imaging section finishes image-shooting.

10 Claims, 4 Drawing Sheets

IMAGING DEVICE AND TRANSMISSION/RECEPTION SYSTEM

BACKGROUND

The present disclosure relates to an imaging device such as a capsule endoscope, which performs transmission and reception of data and the like via radio communication, and to a transmission/reception system using the imaging device.

Recently, research and development of a capsule endoscope have been actively advanced. For example, the capsule endoscope has a capsule of 11 by 26 to 33 mm packaged with a light-sensing chip, a button battery, LED (Light Emitting Diode), CPU (Central Processing Unit), and a radio transmitter. Typically, such a capsule endoscope may shoot 2 to 35 images per second, and may shoot about 50 to 870 thousands of images in examination time of about 8 hours.

Data of the shot images are transferred as a real-time video signal by radio in a megahertz band from the capsule endoscope to an external portable receiver (data logger) via a radio-receiving antenna attached to a subject. Actually, eight or nine patch antennas are attached to a stomach region of the subject, and the image data are stored in a portable receiver carried by the subject.

A transmission/reception system including such a capsule endoscope includes a capsule endoscope as a transmission device introduced into a body cavity of a subject, a reception device for receiving data transmitted from the capsule endoscope, a recording medium in the reception device, and a display device. In the transmission/reception system, data of the internal images of the subject shot by the capsule endoscope are sequentially transmitted by radio in realtime, the data received via the plurality of antennas attached to the stomach region of the subject are recorded into the recording medium in the reception device, and after the data are acquired, the recording medium is transferred into a display device, or the data are displayed through cable communication or wireless communication (for example, see Japanese Unexamined Patent Application Publication No. 2009-189475 or No. 2009-153617). In addition, a system has been developed, where general-purpose PC (Personal Computer) acquires image data from a portable medical device via an insulation-compensating cable communication adaptor device using USB (Universal Serial Bus), a photocoupler, or a transformer (for example, see Japanese Unexamined Patent Application Publication No. 2009-178234).

However, these transmission/reception systems are expensive. In addition, since the antennas and the receiver are attached to a subject body, the subject has been significantly restricted in motion, leading to burden on the subject. Furthermore, the quantity of data transmission is limited, and image-shooting data may become imperfect in a portion such as an esophagus, through which the capsule endoscope moves fast. Moreover, since the transmission/reception systems are low in reception sensitivity, further development has been demanded

SUMMARY

On the other hand, a memory-incorporated capsule endoscope has been developed, where a recording section (memory) is provided in the capsule endoscope, and data of shot images are recorded in the memory, eliminating need of the antennas attached to a subject or need of the data logger carried by the subject.

When the memory-incorporated capsule endoscope is orally taken by a subject, the endoscope starts image-shooting and examination. When the capsule endoscope finishes the image-shooting and examination, the endoscope is excreted from a subject body. When the capsule endoscope is excreted from the subject, a capsule case of the endoscope is torn, and then data are transferred to a host computer through probing of a memory board.

However, such a method where the capsule case is torn and then data are transferred to the host computer through probing of the memory board needs time for tearing the capsule case, and besides has a possibility that data have not been perfectly transferred due to bad contact or electrostatic breakdown in probe connection. Such a difficulty is not limitedly occurred in the capsule endoscope. In other words, in the case that a probe is hardly stationed at an observation point for physical or economic reasons or for safety reasons, for example, in the case of data collection by an unmanned probe helicopter or a subsea probe vessel, or in the case that an observation object moves, the difficulty also has occurred in an imaging device that transfers video data or other data from a mainly battery-driven data collection device or from a medium inserted in the device to a host computer or the like in a safe place or an environmentally good place.

It is desirable to provide an inexpensive imaging device that may perform data transmission promptly and easily, and provide a transmission/reception system using the imaging device.

An imaging device according to an embodiment of the disclosure includes an imaging section, a recording section storing data of images shot by the imaging section, a transmission section transmitting the data stored in the recording section to the outside by radio, and a controller controlling the transmission section to start data transmission after the imaging section finishes image-shooting.

A transmission/reception system according to an embodiment of the disclosure includes an imaging device storing data of shot images, and a data-receiving device receiving the data stored by the imaging device, wherein the imaging device is configured of the imaging device according to the embodiment of the disclosure.

In the imaging device according to the embodiment of the disclosure, after the imaging section finishes image-shooting, data transmission by radio is started without extracting the recording section (memory) to the outside.

In the transmission/reception system according to the embodiment of the disclosure, data from the imaging device are transmitted to the data-receiving device.

According to the imaging device of the embodiment of the disclosure and the transmission/reception system having the imaging device, since data stored in the imaging device are transmitted by radio, the recording section (memory) need not be extracted to the outside, making it possible to perform data transmission promptly and easily. Moreover, a contact probe need not be used for data transmission, eliminating imperfect transfer due to bad contact or electrostatic breakdown. Furthermore, stored data are collectively transferred after image-shooting, enabling power saving.

It is to be understood that both the foregoing general description and the following detailed description are exemplary, and are intended to provide further explanation of the technology as claimed.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the technology.

DETAILED DESCRIPTION OF THE PREFERRED EMBODIMENT

Figure 1:
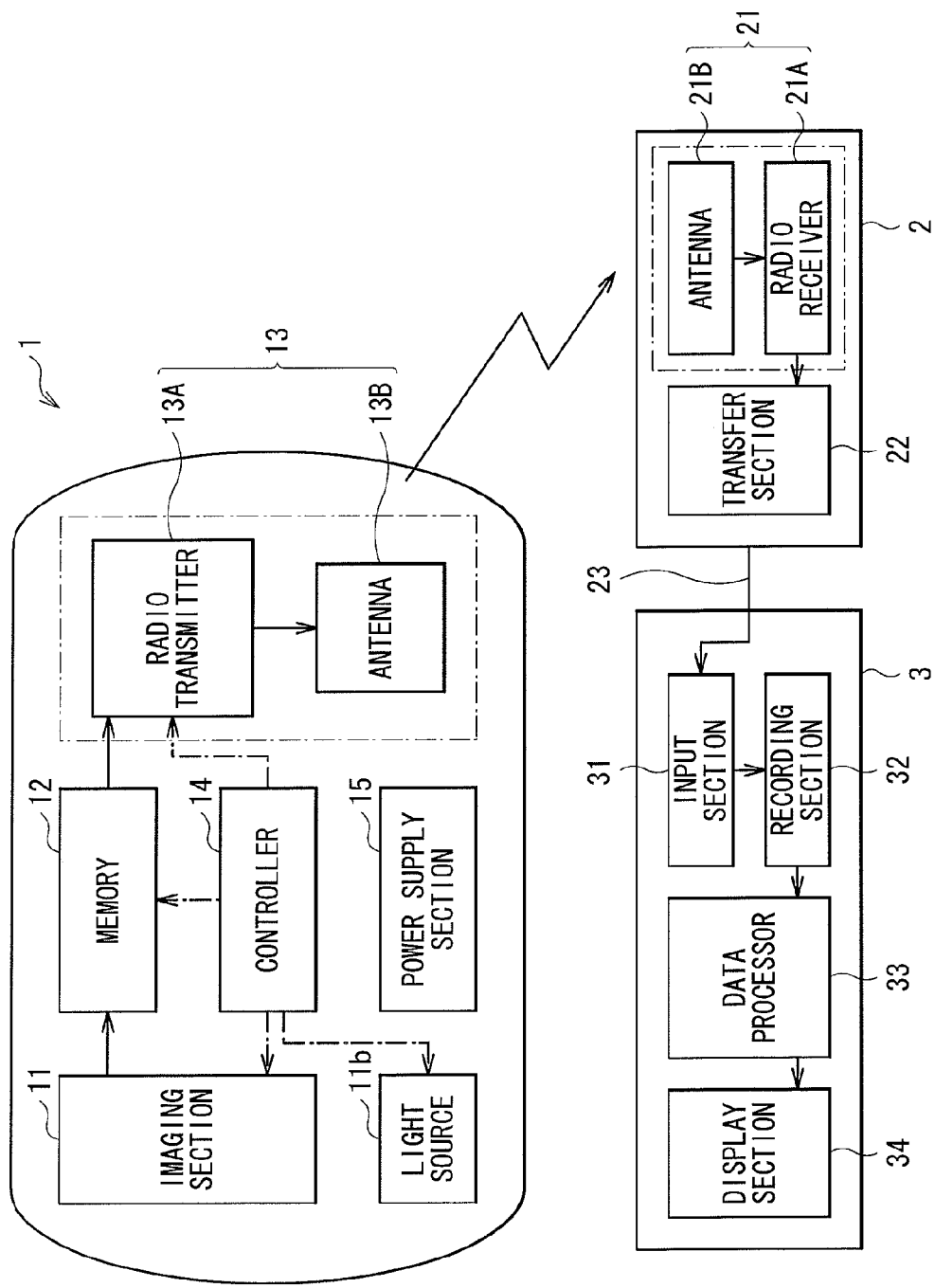
FIG. 1 is a schematic diagram of a transmission/reception system using an imaging device according to an embodiment of the disclosure.

Hereinafter, an embodiment of the disclosure will be described in detail with reference to drawings. Description is made in the following order.
1. Embodiment (example of use of capsule endoscope)
  (1) General Configuration of Transmission/Reception System
  (2) Capsule Endoscope
  (3) Data-Receiving Device
2. Other Application Examples 1. Embodiment (1) General Configuration of System FIG. 1 illustrates a schematic configuration of a transmission/reception system according to an embodiment of the disclosure. The transmission/reception system is configured of an imaging device 1 that acquires data of images of a shooting object or the like, a data-receiving device 2 for receiving data stored by the imaging device 1 and transferring the data, and a host computer 3 that acquires the data transferred from the data-receiving device 2, and performs various kinds of processing of the data, and displays the data.

The imaging device 1 includes an imaging section 11, a recording section (memory) 12 storing data acquired by the imaging section 11, a transmission section 13 for transmitting the data stored in the recording section 12 to the outside, a controller 14 for controlling operation (image-shooting, data-storing, or transmission) of each of the imaging section 11, the recording section 12, and the transmission section 13, a light source 11b for illumination, and a power supply section 15 for supplying power to each section. The transmission section 13 is configured of a radio transmitter 13A and a transmission antenna 13B. Specifically, the power supply section 15 is, for example, a magnetic-electric energy conversion coil, but may be a built-in button battery.

Figure 3:
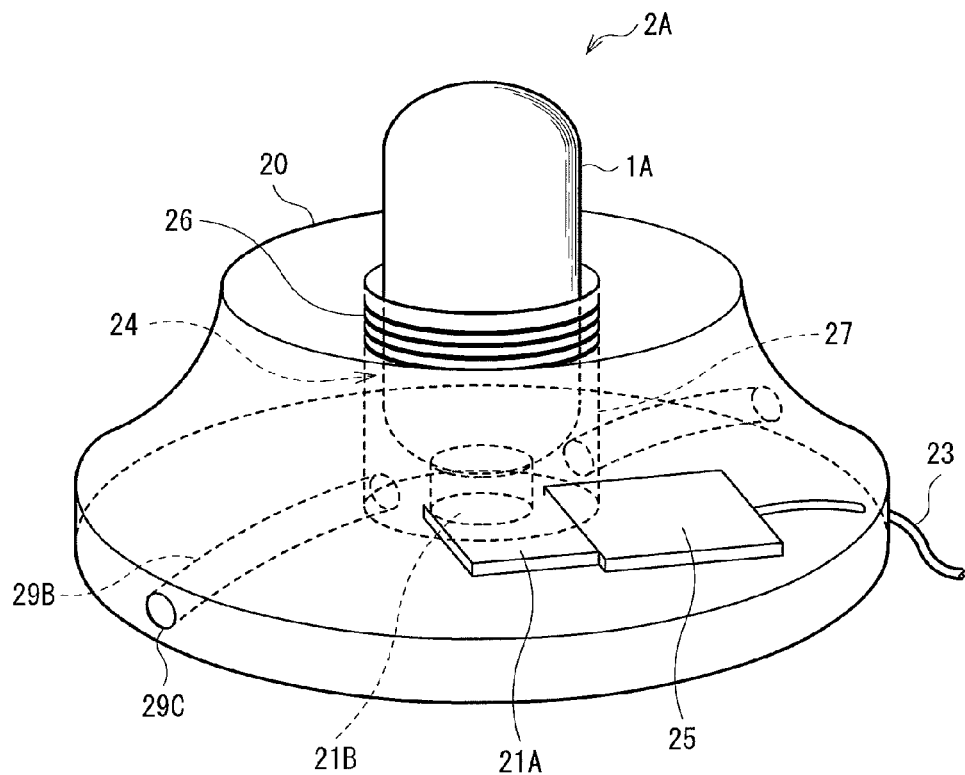
FIG. 3 is a perspective diagram illustrating a configuration of a data-receiving device.

The data-receiving device 2 includes, for example, a reception section 21 receiving data transmitted by radio from the imaging device 1, and a transfer section 22 for transmitting the data received by the reception section 21 to the host computer 3 via a cable 23. The data may be transferred to the host computer 3 by radio. The reception section 21 is configured of a reception antenna 21B and a radio receiver 21A. When the power supply section 15 in the imaging device 1 is configured of a magnetic-electric energy conversion coil, the data-receiving device 2 includes a power transmission coil 26 (FIG. 3). Power is thus supplied by radio from the data-receiving device 2 to the imaging device 1.

The host computer 3 confirms correctness of the data transferred from the data-receiving device 2 and then acquires the data, and performs various kinds of processing of the data, and displays the data. In the host computer 3, the data from the data-receiving device 2 are sequentially stored into a recording section (memory) 32 via an input section 31. The data stored in the recording section 32 are subjected to various kinds of processing by a data processor 33 and then outputted to a display section 34.

For the transmission/reception system, in the imaging device 1, the imaging section 11 shoots images of an object and data of the images are sequentially stored into the recording section 12 under control of the controller 14. After the image-shooting is finished, the radio transmitter 13A transmits the data by radio to the data-receiving device 2 via the transmission antenna 13B. The data transmitted to the data-receiving device 2 are transferred to the host computer 3 via the cable 23. In the host computer 3, the data are sequentially stored into the recording section 32, and then the data are subjected to predetermined processing by the data processor 33 and then displayed by the display section 34.

In the embodiment, data transmission from the imaging device 1 to the data-receiving device 2 and in turn to the host computer 3 is automatically started according to a predetermined procedure at a point when the imaging device 1 is made sufficiently close to the data-receiving device 2 to allow radio transmission. The data transmission may be started according to an instruction from the host computer 3 after the imaging device 1 is made sufficiently close to the data-receiving device 2 to allow radio transmission.

Hereinafter, an example of a transmission/reception system using a capsule endoscope 1A as the imaging device 1 is described as a specific example of the transmission/reception system.

(2) Capsule Endoscope

Figure 2:
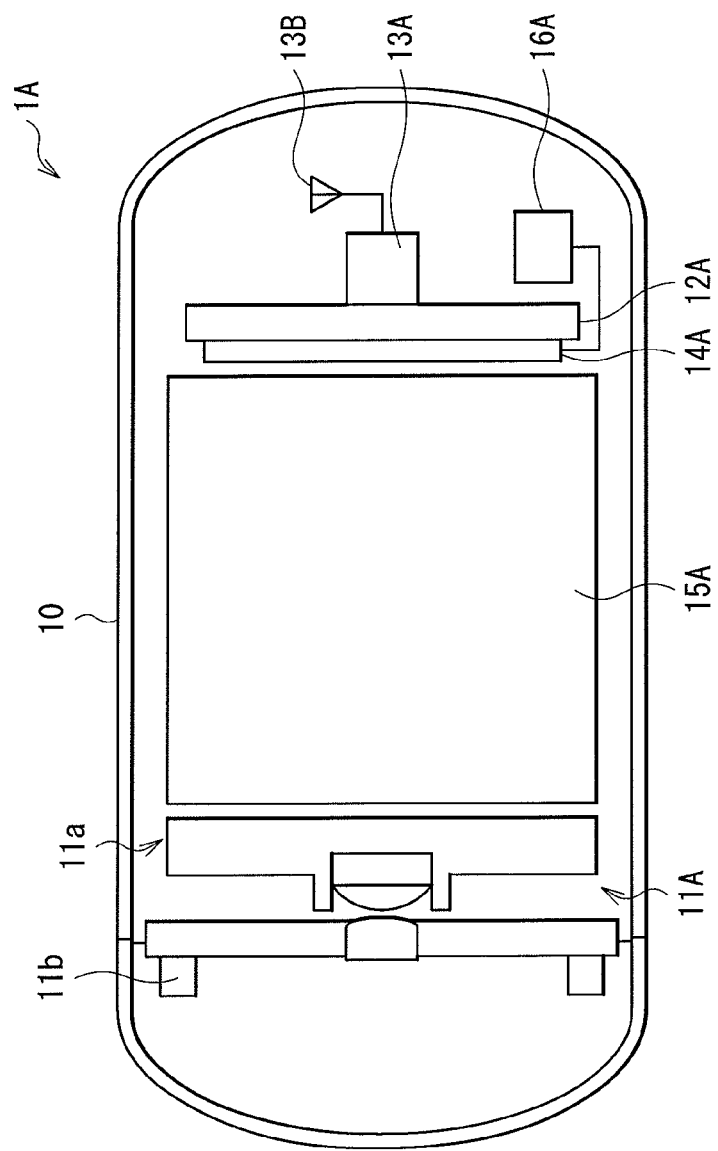
FIG. 2 is a section diagram illustrating a specific configuration of the imaging device.

FIG. 2 illustrates a sectional configuration of the capsule endoscope 1A as an example of the imaging device 1. The capsule endoscope 1A includes a camera (subminiature camera) 11A for shooting images of the inside of a body cavity in a housing 10 having, for example, hemispherical, two end-faces and a cylindrical central-portion. The housing 10 further contains a memory 12A for recording data of images shot by the camera 11A, and the radio transmitter 13A for transmitting the recorded image data to the outside via the antenna 13B after the capsule endoscope 1A is excreted from a subject body.

The housing 10 further contains CPU (Central Processing Unit) 14A and a coil (magnetic force-electric current conversion coil) 15A. The CPU 14A controls image-shooting by the camera 11A and data storing into the memory 12A, and controls data transmission by the radio transmitter 13A from the memory 12A to the data-receiving device 2 (data transfer pad 2A) outside the housing 10. The coil 15A supplies power to the camera 11A, the memory 12A, the radio transmitter 13A, the antenna 13B, and light sources 11b described later, respectively. The housing 10 further contains a sensor (in this case, a reed switch 16A) such as magnetic (reed) switch or magnetic sensor in order to sense setting of the capsule endoscope 1A when the capsule endoscope is set into the data transfer pad 2A as described later. At a point when the reed switch 16A senses the setting of the capsule endoscope into the data transfer pad 2A and thus data transmission is enabled, the CPU 14A allows the coil 15A to supply power to the radio transmitter 13A.

For example, the camera 11A has an objective optical-system such as a lens 11a for shooting images of the inside of a body cavity or the like and has a plurality of (here, two) light sources 11b for illuminating the inside of the body cavity.

Specifically, for example, the camera 11A is configured of CMOS (Complementary Metal Oxide Semiconductor) sensors or CCD (Charge Coupled Device) having LEDs (Light Emitting Diodes) as the light sources 11b.

For example, the memory 12A is a storage element allowing data to be written or erased to/from the element. The CPU 14A, which controls total operation of the capsule endoscope 1A as described before, particularly controls operation of the radio transmitter 13A and power supply thereto such that data stored in the memory 12A is started to be transmitted to the data-receiving device 2 at a point when the capsule endoscope 1A is extracted from a subject and then set in the data-receiving device 2 (data transfer pad 2A). In other words, in the embodiment, data of images shot by the camera 1A are collectively transmitted outside a subject body after image-shooting is finished instead of sequentially transmitting the data in realtime.

The coil 15A converts an external magnetic-field to an electric current and thus supplies power to each section as described before. While the capsule endoscope 1A stays within the subject body, the coil 15A converts a magnetic field emitted from an external magnetic-field generator (not shown) to an electric current so that power is maintained. After the capsule endoscope 1A is excreted from the body, power is supplied to the coil 15A from a power transmission coil 26 in the data transfer pad 2A as described later.

The housing 10 includes one hemispherical end-face formed of a transparent plastic dome, and includes other portions formed of, for example, silicon containing substantially no metal and carbon or of plastic.

(3) Data-Receiving Device

Figure 4:
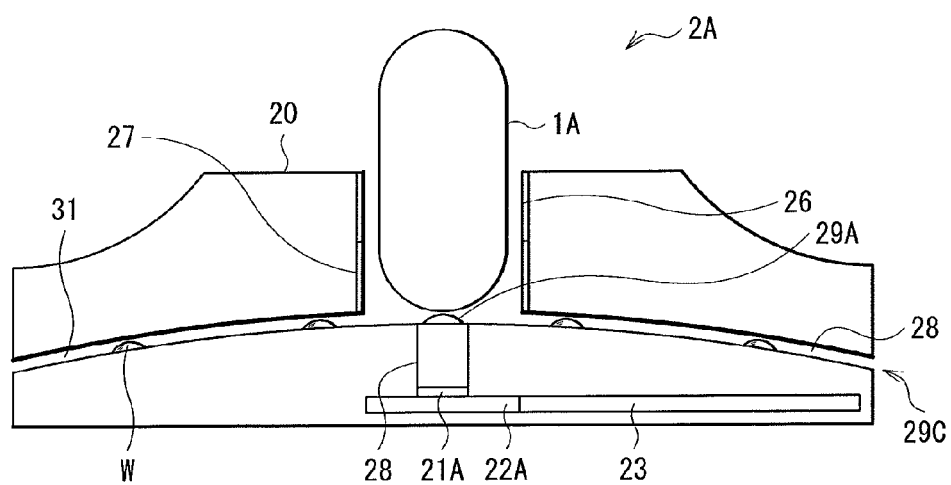
FIG. 4 is a section diagram of the data-receiving device.

FIG. 3 illustrates a perspective configuration of the data transfer pad 2A as an example of the data-receiving device 2 in a see-through manner. FIG. 4 illustrates a sectional configuration of the data transfer pad 2A. The data transfer pad 2A has a pedestal-like housing 20 having an insertion port 24 in the center of the housing for setting the capsule endoscope 1A. The radio receiver 21A having the reception antenna 21B is provided below the insertion port 24. The radio receiver 21A is connected to the host computer 3 via an interface 25 and the cable 23. The power transmission coil 26 is provided on an inner wall surface of the insertion port 24. The power transmission coil 26 is used as a noncontact power supply source to the capsule endoscope 1A during data transmission. When the capsule endoscope 1A has an internal battery, the power transmission coil 26 need not be provided.

A shield 27 may be provided below the power transmission coil 26 on the wall surface of the insertion port 24 in order to block a high-frequency signal or a radiation signal as necessary. In addition, a waveguide 28 may be provided as necessary between the antenna 13B of the capsule endoscope 1A and the reception antenna 21B of the data transfer pad 2A.

The capsule endoscope 1A is removably set in the insertion port 24 with a side of the radio transmitter 13A having the antenna 13B down. A projection 29A is provided in a bottom of the insertion port 24 so that a lower end of the capsule endoscope 1A contacts the projection 29A. A plurality of, for example, two, drains 29C are provided at opposite positions in a side face of the housing 20, and drainage canals 29B are provided between the drains 29C and the projection 29A, respectively. Each drainage canal 29B is sloped so as to gradually fall from a contact point between the capsule endoscope 1A and the data transfer pad 2A, namely, from the projection 29A to each drain 29C. In other words, the data transfer pad 2A has the projection 29A, the drainage canals 29B, and the drains 29C so as to effectively discharge water droplets w adhered to the capsule endoscope 1A during washing, preventing formation of a water film on the capsule endoscope 1A.

Next, operation of the transmission/reception system using the capsule endoscope 1A is described.

When the capsule endoscope 1A is swallowed by a subject, the capsule endoscope starts image-shooting under control of the CPU 14A while staying in a body cavity. First, the light sources (LED) 11b illuminate light to a body cavity wall in response to power supplied from the coil 16A. Next, light reflected by the body cavity wall is captured by the camera 11A through the lens 11A, so that image data are formed. The image data are sent to the memory 12A and stored therein. After the capsule endoscope 1A is excreted from the subject, the radio transmitter 13A in the capsule endoscope 1A transmits by radio the image data stored in the memory 12A to the data transfer pad 2A via the transmission antenna 13B.

Figure 5:
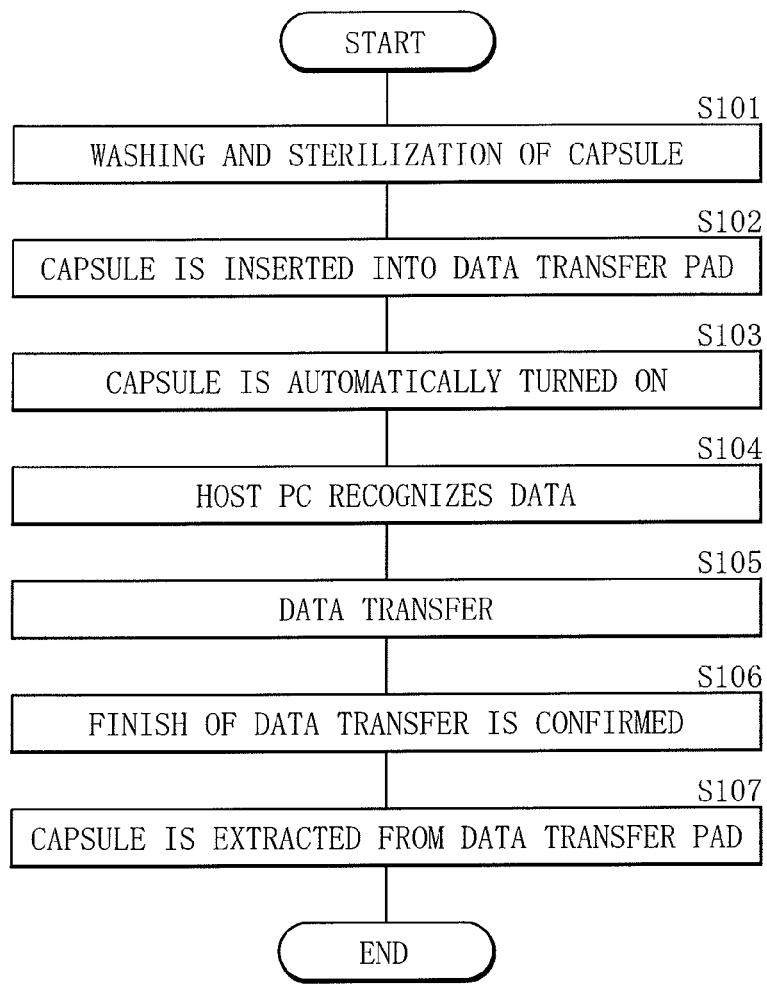
FIG. 5 is a flowchart illustrating operation of the transmission/reception system in data transmission.

FIG. 5 illustrates data transfer processing after the capsule endoscope 1A is excreted from the subject body. First, the capsule endoscope 1A excreted from the subject is washed and sterilized by rinsing or the like (step S101), and then inserted into the insertion port 24 of the data transfer pad 2A with a transmission antenna 13B side down so that the transmission antenna 13B is close to the reception antenna 21B (step S102).

When the capsule endoscope 1A is inserted into the data transfer pad 2A, the sensor 16A in the capsule endoscope 1A detects a magnetic filed from the data transfer pad 2A, so that the capsule endoscope 1A is automatically turned on (step S103). In response, a confirmation signal is sent from the data transfer pad 2A to the host computer 3. Next, the host computer 3 determines setting of the capsule endoscope 1A in the data transfer pad 2A and correctness of data from the capsule endoscope 1A. When the host computer 3 recognizes the data to be correct, preparation of data transfer is completed (step S104).

Next, data transfer is started to the host computer 3 via the data transfer pad 2A (step S105). Specifically, data transmission is started from the memory 12A by the radio transmitter 13A, and the transmitted data are received by the radio receiver 21A of the data transfer pad 2A via the transmission antenna 13B and the reception antenna 21B. The data received by the radio receiver 21A are transmitted by the transfer section 22 to the host computer 3 via the cable 23. The host computer 3 confirms reliability of the transferred data and allows the display section 34 to display end of data transmission (step S106). Finally, the capsule endoscope 1A is extracted from the data transfer pad (step S107).

In the previous transmission/reception system using the capsule endoscope, data of images shot within a body cavity are sequentially recorded in realtime into a portable receiver (data logger) worn by a subject via a plurality of antennas attached to predetermined positions of a subject body as described before. The antennas and the receiver are attached to the subject body in this way, causing burden on the subject, including restriction in motion. In the memory-incorporated capsule endoscope, the capsule excreted from a subject body is torn and data are transferred via a cable host interface, which has resulted in time for tearing the capsule, and in a possibility of imperfect transfer of data due to bad contact or electrostatic breakdown in probing.

In contrast, in the transmission/reception system of the embodiment, the capsule endoscope 1A has the memory 12A for recording data of shot images and the radio transmitter 13A for transmitting the data to the outside by radio. This eliminates need of a plurality of antennas attached to a subject and need of a portable receiver worn by the subject. Moreover, data are transmitted and received by radio, making it possible to collect data without tearing a capsule of the capsule endoscope 1A. Furthermore, data are transmitted and received outside a subject body, enabling use of a high-frequency wave such as millimeter wave which greatly attenuates within a human body. Moreover, data are collectively transmitted after image-shooting is finished, enabling power saving compared with a case where a capsule endoscope continuously communicates with an external data logger.

As described hereinbefore, in the transmission/reception system of the embodiment, the memory 12A is provided in the imaging device 1 (capsule endoscope 1A), and thus data of shot images are collected after the capsule endoscope 1A is excreted from a subject body, making it possible to reduce burden on a subject. Moreover, image data are transmitted and received by radio, which eliminates time for tearing a capsule, making it possible to transfer data promptly and easily after image-shooting and examination. Furthermore, the CPU 14A, which controls transmission of image data, needs to control the radio transmitter 13A only during data transfer after the capsule endoscope 1A is excreted from the subject body, namely, only for a short period compared with the real-time radio transmission in the past, enabling power saving. This allows reduction in size of the coil 15A (or a battery) as the power supply section 15 in the capsule endoscope 1A, enabling reduction in size of the capsule endoscope 1A itself.

Moreover, image data are transmitted and received outside the subject body, enabling use of a high-frequency wave such as millimeter wave for data transfer. This principally makes it possible to transfer image data at a transfer rate about 2000 times as high as a transfer rate of the capsule endoscope in the past. Specifically, a high-frequency wave of 60 GHz with a band width of 7 to 9 GHz is used, making it possible to easily achieve fast transmission in Gbps with an extremely low possibility of interference with another system. Moreover, the wave has a short wavelength, about 5 mm, enabling reduction in size of the antenna 13B or 21A and of each circuit. This allows data transmission with power being saved for extremely-short-distance wireless communication. Specifically, power is 29 mW on a transmission side for communication using simple monopole antennas with a communication distance of 14 mm.

Moreover, data transfer may be performed in a noncontact manner, making it possible to reduce trouble such as bad contact or electrostatic breakdown and reduce operation miss. Furthermore, a capsule need not be torn, which makes it possible to simplify washing-and-sterilization operation of the capsule, and facilitates hygiene control. In addition, a capsule structure, which is demanded to have a water proofing property and acid resistance, may be simplified. Furthermore, for a used capsule endoscope 1A, a capsule skin and a battery are simply replaced, while other expensive components such as the optical system, the memory, and the substrate may be reused, enabling reduction in cost.

2. Other Application Examples

Next, application examples of the imaging device 1 and the transmission/reception system of the embodiment are described. While the imaging device 1 has been configured of the capsule endoscope 1A in the embodiment, this is not limitative, and the imaging device 1 may be used for an imaging device that performs image-shooting at a place where the device is hardly stationed at an observation point for physical or economic reasons or for safety reasons, or performs image-shooting of an observation object when the object moves. For example, the imaging device 1 may be mounted in a telemeter used for remote measurement or in a sonde for meteorological observation at high altitude. Alternatively, the imaging device 1 may be mounted in an unmanned helicopter used for observation of a volcano crater or for house map production. The transmission/reception system described in the embodiment may be used for a transmission/reception system of image data even in such cases.

When each of such various imaging devices is mounted in various kinds of equipment such as an unmanned probe helicopter, noncontact data transfer is enabled, which facilitates making design in consideration of durability, a water proofing property, acid resistance, oil resistance, or weather resistance of the equipment. In addition, data may be transferred from a mainly battery-driven data collection device or a medium incorporated in the device to a host computer or the like in a safe place or an environmentally good place.

While the disclosure has been described with the embodiment hereinbefore, the disclosure is not limited to the embodiment, and various modifications and alterations may be made. For example, the data-receiving device 2 may include a transmission/reception switching section for switching between transmission and reception, a signal processor for converting a received signal, or a signal generator for generating a control signal for the capsule endoscope 1A so as to allow bidirectional communication.

The present disclosure contains subject matter related to that disclosed in Japanese Priority Patent Application JP 2010-155045 filed in the Japan Patent Office on Jul. 7, 2010, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A capsule endoscope comprising:
    an imaging section;
    a recording section that stores data of images captured by the imaging section;
    a transmission section that transmits the data stored in the recording section to the outside via radio communication; and
    a controller that controls the transmission section to start data transmission after the capsule endoscope is excreted from a subject body,
    wherein the data stored in the capsule endoscope is transferred to a data-receiving device, and wherein one or more drains and one or more drainage canals of the data-receiving device discharge water droplets adhered to the capsule endoscope.

2. The capsule endoscope according to claim 1,
    wherein the imaging section, the recording section, and the transmission section are provided in a housing of the capsule endoscope.

3. A transmission/reception system comprising:
    an encapsulated imaging device that stores data of captured images, wherein the encapsulated imaging device comprises:
        an imaging section;
        a recording section that stores data of images captured by the imaging section;
        a transmission section that transmits the data stored in the recording section to the outside via radio communication; and a controller that controls the transmission section to start data transmission after the encapsulated imaging device is excreted from a subject body; and a data-receiving device that receives data stored by the encapsulated imaging device and transfers the data, wherein the data-receiving device comprises:

a housing;

one or more drains provided in a side face of the housing; and one or more drainage canals connected to the one or more drains, wherein the one or more drains and the one or more drainage canals discharge water droplets adhered to the encapsulated imaging device.

4. The transmission/reception system according to claim 3, wherein the encapsulated imaging device starts data transmission when the encapsulated imaging device is set at a position allowing the encapsulated imaging device to transmit data to the data-receiving device.

5. The transmission/reception system according to claim 3, further comprising a host computer acquiring data transferred from the data-receiving device, wherein, when the encapsulated imaging device is set at a position allowing the encapsulated imaging device to transmit data to the data-receiving device and receives a transmission instruction from the host computer, the encapsulated imaging device starts data transmission.

6. The transmission/reception system according to claim 3, wherein the data-receiving device has a function of supplying power to the encapsulated imaging device when the encapsulated imaging device is set at a position allowing the encapsulated imaging device to transmit data to the data-receiving device.

7. The transmission/reception system according to claim 3, wherein the data-receiving device further comprises:

an insertion port provided in the housing to allow the encapsulated imaging device to be removably inserted in the insertion port; and a projection provided in a bottom of the insertion port to allow a lower end of the encapsulated imaging device to contact the projection, wherein the one or more drainage canals are sloped from a periphery of the projection to the one or more drains.

8. The transmission/reception system according to claim 7, wherein the data-receiving device further comprises a wireless reception section at a position allowing transmission and reception of data between the wireless reception section and the encapsulated imaging device inserted in the insertion port.

9. The transmission/reception system according to claim 3, wherein the encapsulated imaging device is a capsule endoscope.

10. The capsule endoscope according to claim 1, wherein the transmission section utilizes millimeter waves for the radio communication.

* * * * *